United States Patent
Schwenk et al.

(10) Patent No.: US 10,813,593 B2
(45) Date of Patent: Oct. 27, 2020

(54) USING VISUAL CONTEXT TO TIMELY TRIGGER MEASURING PHYSIOLOGICAL PARAMETERS

(71) Applicant: KONINKLIJKE PHILIPS N.V., Eindhoven (NL)

(72) Inventors: Marcus Schwenk, Stuttgart (DE); Alexander Dubielczyk, Gaertringen (DE); Harald Greiner, Nufringen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 113 days.

(21) Appl. No.: 16/080,696

(22) PCT Filed: Mar. 22, 2017

(86) PCT No.: PCT/EP2017/056189
§ 371 (c)(1),
(2) Date: Aug. 29, 2018

(87) PCT Pub. No.: WO2017/162506
PCT Pub. Date: Sep. 28, 2017

(65) Prior Publication Data
US 2019/0090820 A1 Mar. 28, 2019

(30) Foreign Application Priority Data
Mar. 22, 2016 (EP) .................................. 16161522

(51) Int. Cl.
*A61B 5/00* (2006.01)
*G06K 9/00* (2006.01)
(Continued)

(52) U.S. Cl.
CPC .......... *A61B 5/7207* (2013.01); *A61B 5/0022* (2013.01); *A61B 5/1113* (2013.01);
(Continued)

(58) Field of Classification Search
USPC ........ 382/100, 103, 106–107, 128–134, 168, 382/172, 181, 199, 219, 224, 232, 254,
(Continued)

(56) References Cited

U.S. PATENT DOCUMENTS 9,830,951 B2 * 11/2017 Bose .................. A63B 24/0062
2011/0137135 A1 * 6/2011 McGrath ................ G16H 40/67
600/301
(Continued)

FOREIGN PATENT DOCUMENTS

GB 2310377 8/1997

*Primary Examiner* — Seyed H Azarian (57) ABSTRACT

Systems and methods for automatically performing one or more physiological measurements. In various embodiments, image and audio data of a setting in which a patient is present may be acquired via one or more recording devices (102). A determination may be made based on the acquired image and audio data of a state of activity associated with the patient. Based on the determined state of activity associated with the patient, a corresponding one or more physiological measurements of the patient to be obtained may be identified. One or more health sensors (122) may then be caused to be operated to obtain the corresponding one or more physiological measurements.

12 Claims, 4 Drawing Sheets (51) Int. Cl.
    *A61B 5/11*           (2006.01)
    *G16H 40/63*       (2018.01)
    *G16H 30/20*       (2018.01)
    *G06T 7/20*         (2017.01)

(52) U.S. Cl.
    CPC .......... *A61B 5/1116* (2013.01); *A61B 5/1118* (2013.01); *A61B 5/1128* (2013.01); *A61B 5/721* (2013.01); *A61B 5/7285* (2013.01); *A61B 5/74* (2013.01); *A61B 5/746* (2013.01); *G06T 7/20* (2013.01); *G16H 30/20* (2018.01); *G16H 40/63* (2018.01); *A61B 2560/0209* (2013.01); *A61B 2560/0242* (2013.01); *A61B 2562/0219* (2013.01)

(58) Field of Classification Search
    USPC .............. 382/274–276, 305, 312; 378/4, 21; 600/301
    See application file for complete search history.

(56)               References Cited

U.S. PATENT DOCUMENTS

| | | | |
|---|---|---|---|
| 2013/0053653 A1* | 2/2013 | Cuddihy | A61B 5/113 600/301 |
| 2013/0182107 A1 | 7/2013 | Anderson | |
| 2014/0235976 A1 | 8/2014 | Bresch | |
| 2016/0125620 A1* | 5/2016 | Heinrich | A61B 5/1113 382/103 |
| 2017/0103178 A1* | 4/2017 | Heinrich | G16H 40/67 |

* cited by examiner

USING VISUAL CONTEXT TO TIMELY TRIGGER MEASURING PHYSIOLOGICAL PARAMETERS

CROSS REFERENCE TO RELATED APPLICATIONS

This application is the U.S. National Phase application under 35 U.S.C. § 371 of International Application No. PCT/EP2017/056189, filed Mar. 16, 2017, published as WO 2017/162506 on Sep. 28, 2017, which claims the benefit of European Patent Application Number 16161522.4 filed Mar. 22, 2016. These applications are hereby incorporated by reference herein.

BACKGROUND OF THE INVENTION

In many healthcare facilities such as hospitals, nursing homes, and clinics, patient monitoring systems are used to observe and analyze the patient's health condition or status. For example, the patient's vital signs can be continuously monitored using various medical devices and also continuously displayed through a patient monitor. Patient monitoring systems may also include alert systems that provide audible or visual notifications when monitored patient vital signs exceed predefined threshold ranges.

To improve their efficacy and usefulness, patient monitoring systems ideally should ensure the accuracy of physiological measurements. Thus, compliance with medical protocols when conducting physiological measurements must be ensured to prevent mistakes when diagnosing or treating a patient's health condition. Typical medical protocols include monitoring the proper use of a medical device by a recognized and authorized medical personnel. To further improve the accuracy of physiological measurements, any motion artifacts detected from the patient's posture and movement should also be included in the data analysis.

G.B. Pat. App. No. 2310377 discloses an image recognition system that acquires user images using an imaging device from which the image recognition system extracts information related to user's hand movements and facial expressions and also determines a user's physiological condition.

SUMMARY OF THE INVENTION

The present disclosure relates to systems and methods for automatically performing one or more physiological measurements.

According to first aspect of the invention, the computer-implemented method for automatically performing one or more physiological measurements, comprises: acquiring, by one or more processors via one or more recording devices image and audio data of a setting in which a patient is present; determining, by the one or more processors based on the acquired image and audio data, a state of activity associated with the patient, identifying by the one or more processors based on the determined state of activity associated with the patient, a corresponding one or more physiological measurements of the patient to be obtained; and causing, by the one or more processors, one or more health sensors to be operated to obtain the corresponding one or more physiological measurements. According to an embodiment the causing comprises providing, by the one or more processors at an output device output to prompt medical personnel to operate the one or more health sensors to obtain the corresponding one or more physiological measurements. According to further embodiment the causing comprises transmitting, by the one or more processors via a communication module, to a notification device, a command configured to cause the notification device to prompt medical personnel to operate the one or more health sensors to obtain the corresponding one or more physiological measurements. In another embodiment the causing comprises automatically operating the one or more health sensors to obtain the corresponding one or more physiological measurements. In a further embodiment the automatically operating comprises transmitting, by the one or more processors through a communication module, one or more commands configured to cause the one or more health sensors to obtain the one or more physiological measurements. According to further embodiment determining the state of activity comprises performing image processing on the acquired image data to identify motion undertaken by the patient.

According to a second aspect of the invention the system for obtaining one or more physiological measurements comprises: one or more recording devices to acquire image data of a setting in which a patient is present; one or more health sensors to obtain one or more physiological measurements from the patient; and a patient monitoring device operably coupled with the one or more recording devices and the one or more health sensors, the patient monitoring device to: perform image processing on the acquired image data; determine, based on the image processing, a state of activity associated with the patient; select one or more physiological measurements to be obtained from the patient based on the determined activity state; and cause the one or more health sensors to be operated to obtain the corresponding one or more physiological measurements. According to an embodiment the system, further comprises an output device, wherein the patient monitoring device is further configured to provide, at the output device, output to prompt medical personnel to operate the one or more health sensors to obtain the corresponding one or more physiological measurements.

According to further embodiment the system comprises a notification device (124), wherein the patient monitoring device is further configured to transmit, to the notification device, a command configured to cause the notification device to prompt medical personnel to operate the one or more health sensors to obtain the corresponding one or more physiological measurements.

In another embodiment the patient monitoring device is further configured to automatically operate the one or more health sensors to obtain the corresponding one or more physiological measurements.

BRIEF DESCRIPTION OF THE DRAWINGS

The accompanying drawings, which are included to provide a further understanding of the disclosure, are incorporated herein to illustrate embodiments of the disclosure. Along with the description, they also serve to explain the principle of the disclosure. In the drawings.

DETAILED DESCRIPTION OF EMBODIMENTS

The present disclosure relates to a system for automatically performing one or more physiological measurements comprising: one or more recording devices to acquire image data of a setting in which a patient is present; one or more health sensors to obtain one or more physiological measurements from the patient; and a patient monitoring device operably coupled with the one or more recording devices and the one or more health sensors. In various embodiments, the patient monitoring device may be configured to: perform image processing on the acquired image data; determine, based on the image processing, a state of activity associated with the patient; select one or more physiological measurements to be obtained from the patient based on the determined activity state; and cause the one or more health sensors to be operated to obtain the corresponding one or more physiological measurements.

The present disclosure also relates to a method for automatically performing one or more physiological measurements comprising: acquiring, via one or more recording devices, image and audio data of a setting in which a patient is present; determining, based on the acquired image and audio data, a state of activity associated with the patient; identifying, based on the determined state of activity associated with the patient, a corresponding one or more physiological measurements of the patient to be obtained; and causing one or more health sensors to be operated to obtain the corresponding one or more physiological measurements.

In one embodiment of the present disclosure, the recording device may begin capturing image and sound data at a preset time based on one or more records of a schedules database. The image and sound data may be sent to and stored in the patient monitoring device. The patient monitoring device may compare (e.g., using various imaging processing techniques) the acquired image and audio data with the image data, object data, and sound data stored in a personnel and patients database, an objects database, and a sounds database, respectively. This comparison allows the patient monitoring device to determine the patient's activity state. Following this, the patient monitoring device confirms if the determined patient's activity state matches a predetermined activity state stored in the schedules database. Once confirmed, the patient monitoring device determines a physiological measurement to be performed and subsequently triggers a health sensor to perform the determined physiological measurement.

Figure 1:
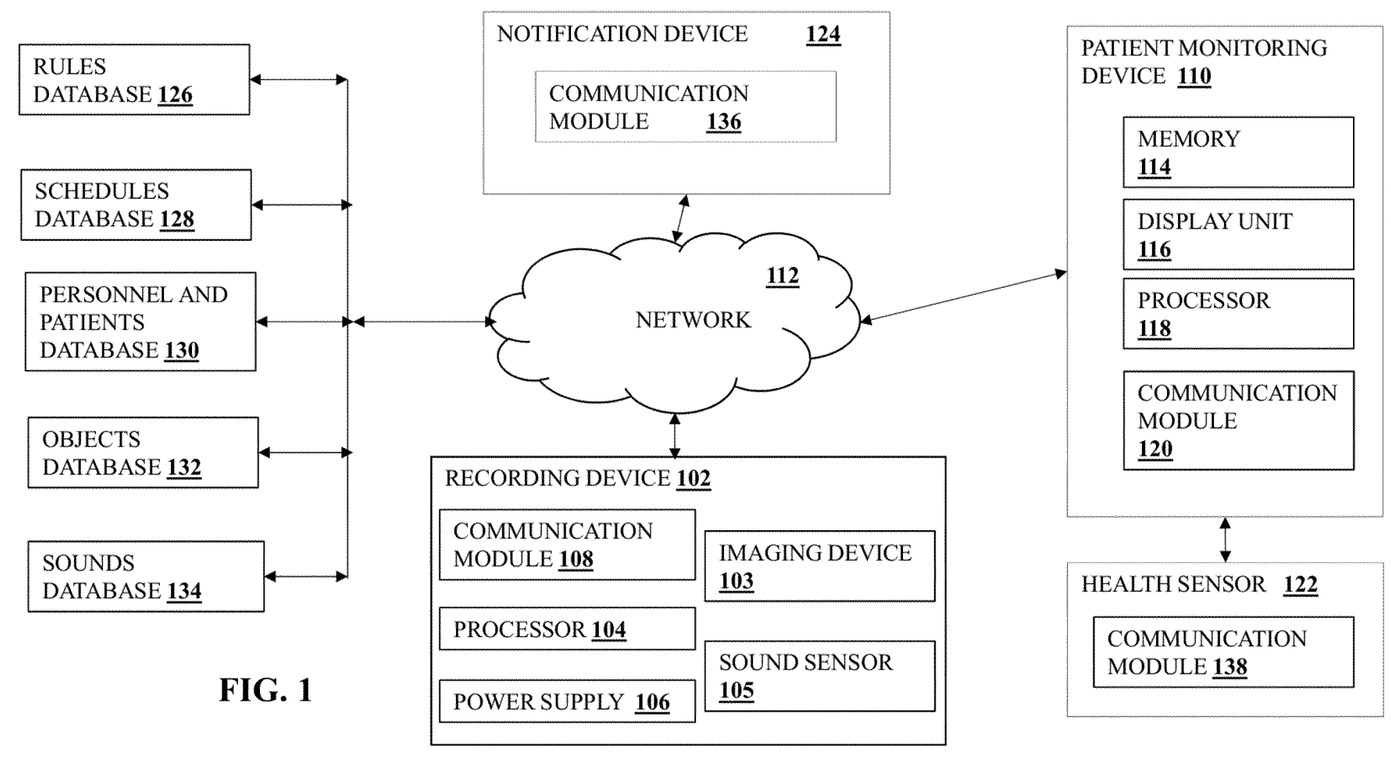
FIG. 1 illustrates a system for automatically performing one or more physiological measurements according to various embodiments of the present disclosure.

FIG. 1 illustrates an example system configured with selected aspects of the present disclosure to automatically performing one or more physiological measurements based on a patient's activity state. As shown, the system may include one or more recording devices 102 which each may include, operably coupled with one or more processors 104, an imaging device 103, a sound sensor 105, a power supply 106, and a communication module 108 that facilitates communication with a patient monitoring device 110 through one or more networks 112. The patient monitoring device 110—which may include a memory 114, a display unit 116, one or more processors 118, and a communication module 120—communicates with a health sensor 122 and a notification device 124. The patient monitoring device 110 is also in communication with a rules database 126, a schedules database 128, a personnel and patients database 130, an objects database 132, and a sound database 134. The databases (126, 128, 130, 132, and 134) may reside within the patient monitoring device 110, each may be a stand-alone device connected to the patient monitoring device 110 through the cloud or a network 112, or they may distributed in various ways among multiple computing devices (e.g., a server farm).

The term "health sensor" as used herein (e.g., to 122) refers to any device, instrument, equipment, or apparatus capable of measuring a physiological parameter or assisting in the diagnosis of a physiological condition or disease. Examples of health sensors that may be used according to various embodiments of the present disclosure include, but are not limited to, pulse oximeters, blood pressure cuffs, body temperature sensors, and other sensors capable of detecting pulse rate, electrocardiograph patterns, heart rate, blood alcohol content, respiratory rate, blood oxygen saturation level, galvanic skin response, and glucose level.

The term "imaging device" as used herein (e.g., at 103) refers to any device capable of capturing, recording, or storing an image, video, and other forms of digital or electronic representation of an object or a scene. Imaging devices incorporated into various embodiments may come in various forms in various embodiments. These types are well-known and are available commercially. Commonly used imaging devices are semiconductor charged-coupled devices ("CCD") or active pixel sensors in complementary metal-oxide-semiconductor ("CMOS"). Examples of imaging devices may include digital cameras, video cameras, closed-circuit televisions ("CCTVs"), webcams and smart cameras.

Sound sensor 105 may take various forms, most of which are well-known and are available commercially. Many of these sound sensors are microphone-based. Examples of microphone-based sound sensors are piezoelectric microphones, MEMS microphones, condenser microphones, fiber optic microphones, electret condenser microphones, dynamic microphones, ribbon microphones, carbon microphones, laser microphones, and liquid microphones.

In various embodiments, the rules database 126 may store data and pre-stored parameters corresponding to one or more rules. The rules database 126 also stores corresponding decisions and actions resulting from a comparison of those pre-stored data and parameters with detected, monitored, or measured one or more data and parameters. In various embodiments, the schedules database 128 may store information, data and pre-stored parameters corresponding to the schedules of one or more actions, events, tasks, and procedures that include one or more physiological measurements.

In various embodiments, the personnel and patients database 130 may store information about and photos and/or videos associated with (e.g., depicting) medical personnel and patients. In various embodiments, the objects database 132 may store images of medical devices, equipment, non-medical devices, and objects found in a medical setting or a patient room. In various embodiments, the sounds database 134 may store sound data associated with medical personnel, patients, visitors, as well as sound data associated with hospital equipment (e.g., what sounds indicate presence of a particular machine?), devices, intercom announcements, and so forth.

In various embodiments, the notification device 124 may be any device capable of sending and receiving alerts or alarms to a person or another device. Examples of notification device are smartphones, personal digital assistants (PDAs), tablets, smart wearable devices such as smart watches and glasses, and so forth. For example, in some embodiments, the notification device 124 may cause one or more messages to be transmitted and/or output to medical personnel to obtain one or more physiological measurements from a patient, e.g., in response to an instruction from the patient monitoring device 110. In some embodiments, the notification device 124 may include a message server (not depicted) configured to cause various types of messages to be provided to various persons at various devices. These messages may take various forms, such as emails, text messages, instant messages, propriety messages, pages, and so forth. In some embodiments, notification device 124 may be omitted, and notifications may be handled by other components, such as the patient monitoring device 110.

In some embodiments, the notification device 124 and health sensor 122 each has their own communication module (136 and 138, respectively). In some embodiments, the recording device 102 and health sensor 122 may be in a low-power state when not activated by the patient monitoring device 102. While in a low-power state, such as in idle or sleep mode, the processors 104 of the recording device 102 and health sensor 122 may turn off the corresponding communication modules (i.e. 108 and 138).

The communication modules 108, 120, 136, 138, may be standalone devices or components of a device that allow communication—e.g., sending and receiving of commands, triggers, notifications, prompts, acknowledgments, information, messages, forms, and various types of data—among the patient monitoring device 110, notification device 124, one or more health sensors 122, and one or more recording devices 102. In accordance with the various embodiments of the present disclosure, each communication module may take the form of any transmitter or receiver configured for use with Wi-Fi, Bluetooth, infrared, NFC, radio frequency, cellular communication, visible light communication, Li-Fi, WiMax, ZigBee, fiber optic and other forms of wireless communication. Alternatively, the communication modules may be physical channels such as USB cables, Ethernet, or other wired forms of communication.

Motion sensors may be used in various embodiments, e.g., as components of patient monitoring device 110, and may be based on infrared, optical, microwave, ultrasonic, acoustic, or tomographic sensors, and those that fall under the category of occupancy sensors. Motion sensors used in accordance with the disclosure may be of passive or dynamic type, or a combination of both. Passive infrared sensors work by detecting heat movement. They comprise a pyroelectric sensor designed to detect infrared radiation radiated by a moving body. When the passive infrared sensor detects body heat movement, the sensor may activate any lighting system connected to it. To minimize the incidences of false alarms, a combination of different types of motion sensors may be used. For example, a combination of infrared and microwave motion sensors may be employed. The infrared sensor's detection of a movement may be used to trigger the microwave sensor, which may require a higher threshold to trip, so that an alarm or alert is triggered only when the microwave sensor also detects motion following the infrared sensor's detection of a movement.

Figure 2:
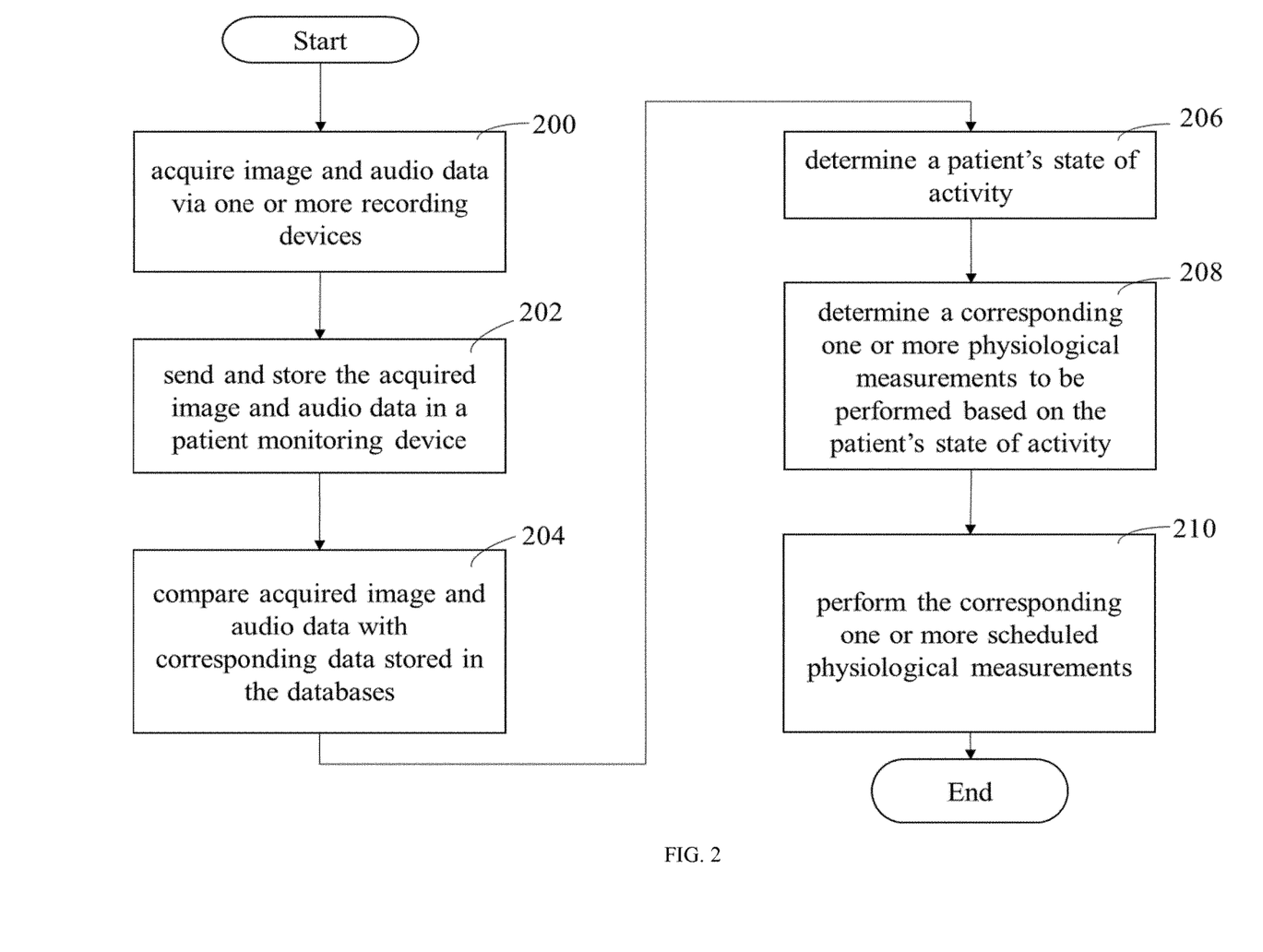
FIG. 2 illustrates a method for automatically performing one or more physiological measurements according to various embodiments of the present disclosure.

FIG. 2 illustrates an example method for automatically performing one or more physiological measurements based on a patient's activity state. At block 200, the one or more recording devices (e.g., 102 in FIG. 1) may acquire image and audio data inside the patient room. At block 202, the acquired data may be sent to and stored in the patient monitoring device (e.g., 110 in FIG. 1). At block 204, the acquired image and audio data may then be compared, e.g., by the patient monitoring device, with the image data, object data, and sound data stored in the personnel and patients database (e.g., 130), objects database (e.g. 132), and sounds database (e.g., 134), respectively.

At block 206, a determination may be made of the patient's activity state and the patient's activity context based on the comparison at block 204. A patient's activity state may include a variety of attributes, e.g., posture, head position, body motion, etc. A patient's activity context may include a variety of activities, such as sleeping, eating, drinking, using a mobile device, watching television, taking medicine, exercising, running, jogging, walking, swimming, etc.

Based on the determined patient's activity context, at block 208, the patient monitoring device may determine one or more physiological measurements to be obtained from the patient. For example, if the patient is determined to have an activity state of immobile and an activity context of sleeping, then one or more physiological measurements that are best taken in such a context—e.g., resting heart rate, blood oxygen saturation level (SpO2), etc.—may be identified. At block 210, the patient monitoring device may trigger the one or more health sensors to perform the corresponding one or more physiological measurements determined at block 208.

Figure 3:
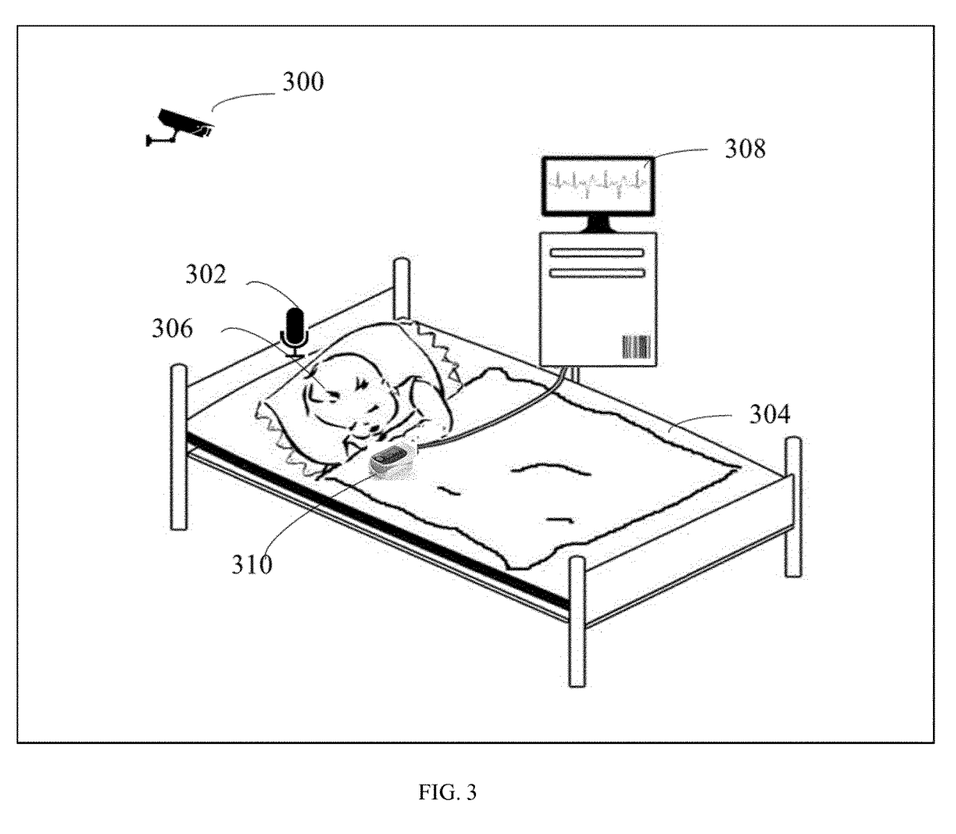
FIG. 3 illustrates an example embodiment of the present disclosure.

In an exemplary embodiment of the present disclosure as illustrated in FIG. 3, an imaging device 300 is strategically placed in one corner of the patient room. Also, a microphone 302 is located on one side of the patient's bed 304 to closely monitor and detect sounds originating from the patient 306—which may include sneezing, snoring, coughing, breathing, mumbling, and screaming, etc. Other types of sounds that may also be monitored and detected are music and sounds coming from a radio, computer, television, laptop, speakers, mobile phone, portable digital assistant ("PDA"), alarm clock, and other devices. The imaging device 300 and the microphone 302 may continuously acquire image and audio data and also continuously send these data to the patient monitoring device 308. By comparing the acquired image and audio data with the image data, object data, and sound data stored in the personnel and patients database (e.g., 130), objects database (e.g., 132), and sounds database (e.g., 134), the patient monitoring device 308 determines that the patient 306 is sleeping steadily with minimal body movement. The patient monitoring device 308 then determines that measuring the patient's SpO2 can be performed given the patient's current activity state. The patient monitoring device 308 thus triggers the pulse oximeter 310 to measure the patient's blood oxygen saturation level.

Figure 4:
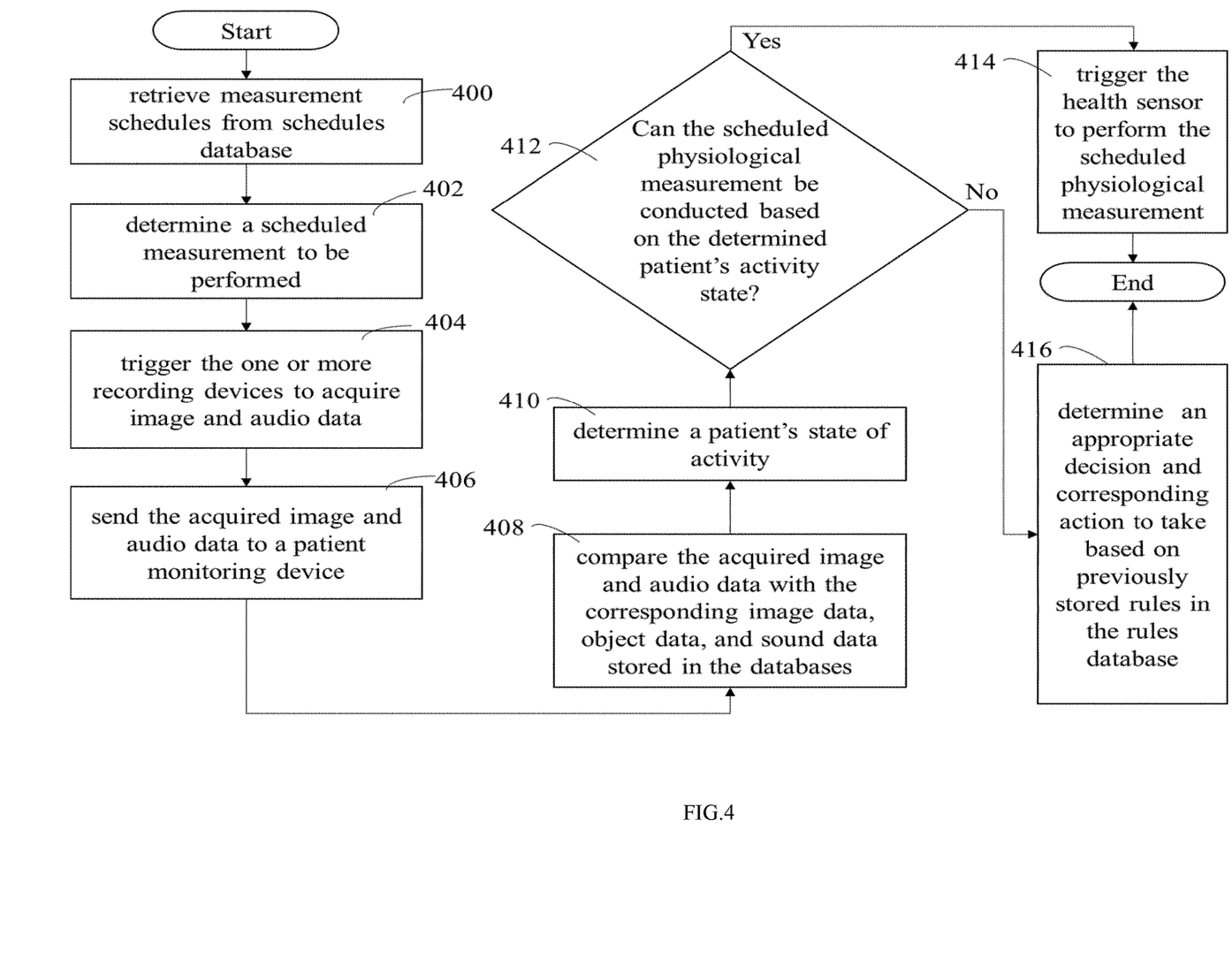
FIG. 4 illustrates a method for automatically performing one or more physiological measurements in accordance with another example embodiment of the present disclosure.

FIG. 4 depicts another example method of performing techniques described herein, in accordance with various embodiments. At block 400, the patient monitoring device (e.g., 110 in FIG. 1) may retrieve measurement schedules from the schedules database (e.g., 128 in FIG. 1). At block 402, the patient monitoring device may determine a scheduled physiological measurement to be performed on a patient. If there is a physiological measurement scheduled in the near future, at block 404, the patient monitoring device may trigger the one or more recording devices (e.g., 102 in FIG. 1) to record image and audio data. At block 406, the recorded image and audio data may be sent to the patient monitoring device. At block 408, the recorded image and audio data may then be compared with the corresponding image data, object data, and sound data stored in the databases. Based on the comparison, at block 410, the patient's activity state may be determined.

At block 412, the patient monitoring device may then check if the scheduled physiological measurement can be conducted based on the determined patient's activity state. For example, if a scheduled physiological measurement involves the measurement of a running person's heart rate and the presently detected activity state is that of a sleeping person, then, the scheduled physiological measurement will not be performed. If the scheduled physiological measurement can be conducted, at block 414, the patient monitoring device may trigger the health sensor (e.g., 122) to perform the scheduled physiological measurement. Back at block 412, if the scheduled physiological measurement cannot be conducted, at block 416, the patient monitoring device may determine what appropriate decision and corresponding action to take based on previously stored rules in the rules database (e.g., 126 in FIG. 1).

As an example scenario in which one or more embodiments of the present disclosure may be employed, suppose an elderly person who is diagnosed with premature ventricular contractions is scheduled to undergo a 24-hour heart rate monitoring for three days in an assisted living facility. Imaging devices, each integrated with a microphone, may be installed in each assisted living facility room. Assume the elderly's heart rate measurement is scheduled to be performed using a wearable heart rate monitor every three hours while the patient is engaged in various activities to determine the patient's heart rate pattern. Here, five minutes before the scheduled heart rate measurement, the one or more imaging devices will scan each assisted living facility room and determine the context of the elderly person's activity state using facial, object, and/or motion recognition.

On the first day of the 24-hour heart rate monitoring of the elderly person and five minutes before the first scheduled heart rate monitoring, the one or more imaging devices may scan each assisted living facility room. Based on image processing of acquired image data, it may be determined that the elderly person is running on a treadmill in the physical activity room. At the scheduled time for the heart rate monitoring after the elderly person is detected, the wearable heart rate monitor may measure the elderly person's heart rate at 93 beats per minute. Three hours after the first scheduled heart rate measurement, the imaging device detects the elderly person playing chess against another elderly person inside the recreational room and then, the wearable heart rate monitor takes a second heart rate measurement. The wearable heart rate monitor measures the elderly person's heart rate at 76 beats per minute. After each measurement, the acquired data may be sent to and stored in a network server. Upon completion of the three-day heart rate monitoring, an authorized doctor may review the elderly person's heart rate data to determine if the elderly person has any potential heart abnormality or disease.

In another example, suppose a patient confined in a hospital room is scheduled to have a fasting blood sugar ("FBS") test. A recording device inside the patient's room may continuously acquire image and/or audio data to effectively monitor the patient 24-hours a day. Suppose that an hour prior to taking the scheduled FBS test, the patient consumed a meal, which is detected and recorded by the recording device. This recorded data from the recording device may then sent be to the hospital's main computer system. The hospital's main computer system may determine that the scheduled FBS test cannot proceed because the patient consumed a meal during the required fasting period of eight hours prior to the scheduled test. In some embodiments, the hospital's main computer system may automatically reschedule the FBS test to another time or date. Optionally, an alert may be raised, e.g., as a message sent to the attending medical personnel to inform him or her about the patient's non-compliance. The medical personnel may manually reschedule the FBS test via the hospital's main computer system.

In another example, suppose a patient's skin conductance is scheduled to be measured at four in the afternoon. Five minutes before the scheduled test, the patient monitoring device may trigger the imaging device to acquire image and audio data. The imaging device may then send the acquired image and audio data to the patient monitoring device. By performing image processing on the acquired image and audio data, the patient monitoring device may detect that the patient is exercising inside the activity room. The monitoring system may then determine whether a skin conductance measurement can be conducted on a person who is exercising based on rules retrieved from the rules database. The patient monitoring device may determine that the scheduled skin conductance measurement cannot proceed according to the rules because sweat can affect the accuracy of a patient's skin conductance measurement. Thus, the patient monitoring device may reschedule the measurement at another time or day. Additionally or alternatively, the patient monitoring device may notify medical personnel that the scheduled skin conductance measurement was not performed because the patient was detected inside the activity room right before the scheduled test.

In another aspect of the present disclosure, a scheduled physiological measurement may still proceed even though the detected patient's activity state does not match the required activity state for a scheduled measurement based on the rules prescribed by the rules database. Here though, the patient monitoring device may also determine the allowed measurement accuracy level for the scheduled measurement. For example, suppose a child is scheduled for an oxygen saturation (SpO2) measurement at midnight, which is the child's predetermined sleeping time. However, suppose the child is experiencing high fever, which causes the child to shake involuntarily and excessively. Despite detecting the child's body movements, the patient monitoring device determines that the amount of movement detected remains within the preset acceptable accuracy level. Hence, the patient monitoring device proceeds to trigger the pulse oximeter to measure the child's SpO2 level. Data corresponding to the acquired SpO2 level, the preset accuracy level, and the detected patient's activity state are then sent to and stored in a network server. In this case, the physiological measurement proceeds according to schedule and the medical personnel is able to analyze and use the patient's physiological data for diagnosis.

In another embodiment of the present disclosure, the one or more physiological measurements may be conducted manually instead of through the patient monitoring device. After identifying the one or more physiological measurements to be performed on a patient, the patient monitoring device (e.g., 110) may send a notification to the medical personnel's notification device. The notification provides instructions to the medical personnel on how to properly conduct the physiological measurement including the correct health sensor to use, the most effective location to place the health sensor on the patient's body, the proper patient body posture for the measurement, the duration of the measurement, etc. In some embodiments, another notification may be transmitted by the monitoring system to the hospital's main computer system when the medical personnel does not comply with the instructions provided.

In another aspect of the present disclosure, the patient monitoring device (e.g., 110 in FIG. 1) may be further connected to a motion sensor such as a gyroscope and/or an accelerometer for detecting the patient's position and movement. The gyroscope and/or accelerometer data may be combined with the imaging device data to accurately determine, monitor, and measure motion parameters relating to the patient such as speed, velocity, acceleration, and a change in the patient's posture or position (e.g., moving from a supine position to a prone position). In some embodiments, the patient monitoring device may execute a measurement adjustment algorithm for filtering and normalizing the physiological measurement values, e.g., to compensate for, reduce, and/or eliminate motion artifacts detected by the accelerometer. This improves the accuracy and precision of the physiological measurement readings gathered by the one or more health sensors.

In accordance with the various aspects of the present disclosure, objects and persons may be identified by the recording device 102 using, for example, pattern recognition, image recognition, image registration, object recognition, facial recognition, feature extraction, color recognition, optical character recognition, motion analysis covering tasks such as egomotion, tracking, and optical flow, pose estimation, machine vision, machine learning, content-based image retrieval, shape recognition, artificial intelligence, neural networks, and other methods of image processing as well as other types of computer vision-based technology.

In some embodiments the system for obtaining one or more physiological measurements may comprise, instead of a recording device, an input for receiving image data (as well as audio data from the microphone 302, for example) of the setting in which the patient is present acquired by one or more recording devices 102. The system may further comprise, instead of a sensor, a sensor input for receiving one or more physiological measurements from the patient obtained one or more health sensors 122. In this embodiment the patient monitoring devices includes a sensor output for controlling the sensors, wherein via said sensor output the patient monitoring device is arranged to cause the one or more health sensors to be operated to obtain the corresponding one or more physiological measurements.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A computer-implemented method for automatically performing one or more physiological measurements, comprising:
    acquiring, by one or more processors via one or more recording devices, image and audio data of a setting in which a patient is present;
    acquiring, by the one or more processors from one or more motion sensors, one or more signals indicative of motion undertaken by the patient;
    determining, by the one or more processors based on the acquired image and audio data, a state of activity associated with the patient;
    identifying, by the one or more processors based on the determined state of activity associated with the patient, a corresponding one or more physiological measurements of the patient to be obtained;
    causing, by the one or more processors, one or more health sensors to be operated to obtain the corresponding one or more physiological measurements; and
    executing, by the one or more processors, a measurement adjustment algorithm to filter and normalize the one or more obtained physiological measurements to reduce or eliminate one or more motion artifacts detected by the one or more motion sensors.

2. The method of claim 1, wherein the causing comprises providing, by the one or more processors at an output device, output to prompt medical personnel to operate the one or more health sensors to obtain the corresponding one or more physiological measurements.

3. The method of claim 1, wherein the causing comprises transmitting, by the one or more processors via a communication module, to a notification device, a command configured to cause the notification device to prompt medical personnel to operate the one or more health sensors to obtain the corresponding one or more physiological measurements.

4. The method of claim 1, wherein the causing comprises automatically operating the one or more health sensors to obtain the corresponding one or more physiological measurements.

5. The method of claim 4, wherein the automatically operating comprises transmitting, by the one or more processors through a communication module, one or more commands configured to cause the one or more health sensors to obtain the one or more physiological measurements.

6. The method of claim 1, wherein determining the state of activity comprises performing image processing on the acquired image data to identify motion undertaken by the patient.

7. A system for obtaining one or more physiological measurements comprising:
    an input for receiving image data acquired by one or more recording devices of a setting in which a patient is present;
    a sensor input for receiving one or more physiological measurements obtained by one or more health sensors from the patient;
    one or more motion sensors for generating one or more signals indicative of motion by the patient; and
    a patient monitoring device operably coupled with the one or more recording devices, the one or more motion sensors, and the one or more health sensors, the patient monitoring device configured to:
    perform image processing on the acquired image data;
    determine, based on the image processing, a state of activity associated with the patient;
    select one or more physiological measurements to be obtained from the patient based on the determined activity state;
    cause the one or more health sensors to be operated to obtain the corresponding one or more physiological measurements; and
    execute a measurement adjustment algorithm to filter and normalize the one or more obtained physiological measurements to reduce or eliminate one or more motion artifacts detected by the one or more motion sensors.

8. The system of claim 7, further comprising an output device, wherein the patient monitoring device is further configured to provide, at the output device, output to prompt medical personnel to operate the one or more health sensors to obtain the corresponding one or more physiological measurements.

9. The system of claim 7, further comprising a notification device, wherein the patient monitoring device is further configured to transmit, to the notification device, a command configured to cause the notification device to prompt medical personnel to operate the one or more health sensors to obtain the corresponding one or more physiological measurements.

10. The system of claim 7, wherein the patient monitoring device is further configured to automatically operate the one or more health sensors to obtain the corresponding one or more physiological measurements.

11. The system of claim 10, wherein the patient monitoring device is further configured to transmit one or more commands configured to cause the one or more health sensors to obtain the one or more physiological measurements.

12. The system of claim 7, wherein the patient monitoring device is further configured to determine perform image processing on the acquired image data to identify motion undertaken the patient.

* * * * *